(12) United States Patent
Jetti et al.

(10) Patent No.: US 8,993,786 B2
(45) Date of Patent: Mar. 31, 2015

(54) CRYSTALLINE FOSAMPRENAVIR CALCIUM AND PROCESS FOR THE PREPARATION THEREOF

(75) Inventors: Ramakoteswara Rao Jetti, Hyderabad (IN); Neelima Bhagavatula, Hyderabad (IN); Asha Rani Gorantla, Hyderabad (IN)

(73) Assignee: Mylan Laboratories Ltd., Hyderabad (IN)

( * ) Notice: Subject to any disclaimer, the term of this patent is extended or adjusted under 35 U.S.C. 154(b) by 0 days.

(21) Appl. No.: 13/983,341

(22) PCT Filed: Feb. 9, 2012

(86) PCT No.: PCT/IN2012/000089
§ 371 (c)(1),
(2), (4) Date: Aug. 2, 2013

(87) PCT Pub. No.: WO2012/107937
PCT Pub. Date: Aug. 16, 2012

(65) Prior Publication Data
US 2013/0317236 A1    Nov. 28, 2013

(30) Foreign Application Priority Data
Feb. 10, 2011 (IN) .............................. 381/CHE/2011

(51) Int. Cl.
*C07F 9/655* (2006.01)
(52) U.S. Cl.
CPC .................................. *C07F 9/65515* (2013.01)
USPC .............................. 549/222; 514/99; 424/400

(58) Field of Classification Search
CPC .................................................... C07F 9/65515
USPC ........................................................... 549/222
See application file for complete search history.

(56) References Cited

U.S. PATENT DOCUMENTS

| 6,514,953 | B1 | 2/2003 | Armitage et al. |
| 2010/0179162 | A1 | 7/2010 | Grant et al. |
| 2011/0165202 | A1 | 7/2011 | Leksic et al. |
| 2011/0224443 | A1* | 9/2011 | Mandava et al. ............. 548/415 |

FOREIGN PATENT DOCUMENTS

WO    WO 2011001383 A1 *  1/2011

OTHER PUBLICATIONS

Armarego, W. L. F., Purification of Laboratory Chemicals, 5th Edition, 2003, Butterworth Heinemann, Chapter 1, p. 1-30).*

* cited by examiner

*Primary Examiner* — Noble Jarrell
*Assistant Examiner* — John Mauro
(74) *Attorney, Agent, or Firm* — Ladas & Parry LLP

(57) ABSTRACT

The main object of the present invention relates to a novel crystalline form of Fosemprenavir Calcium designated as Form A. Another object of the present invention relates to a process for the preparation of Crystalline Form A of Fosemprenavir Calcium. Yet another object of the present invention relates to crystalline Forma A of Fosemprenavir Calcium characterized by a PXRD diffraction having reflections at about 3.1±0.2, 4.4±0.2, 5.0±0.2, 6.3±0.2, 7.4±0.2, 8.0±0.2, 2θ.

13 Claims, 4 Drawing Sheets

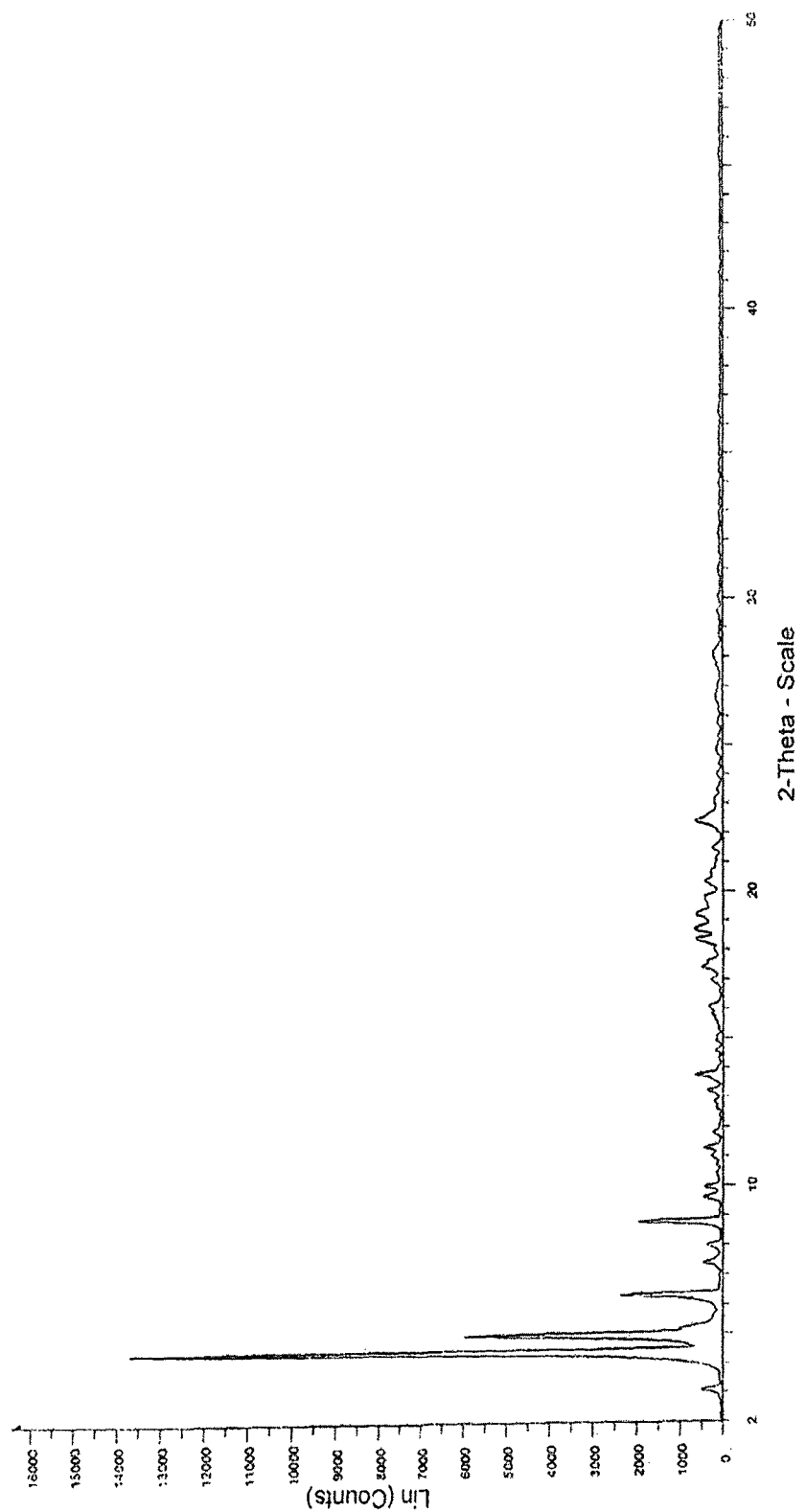
Fig. 1 (Form A)

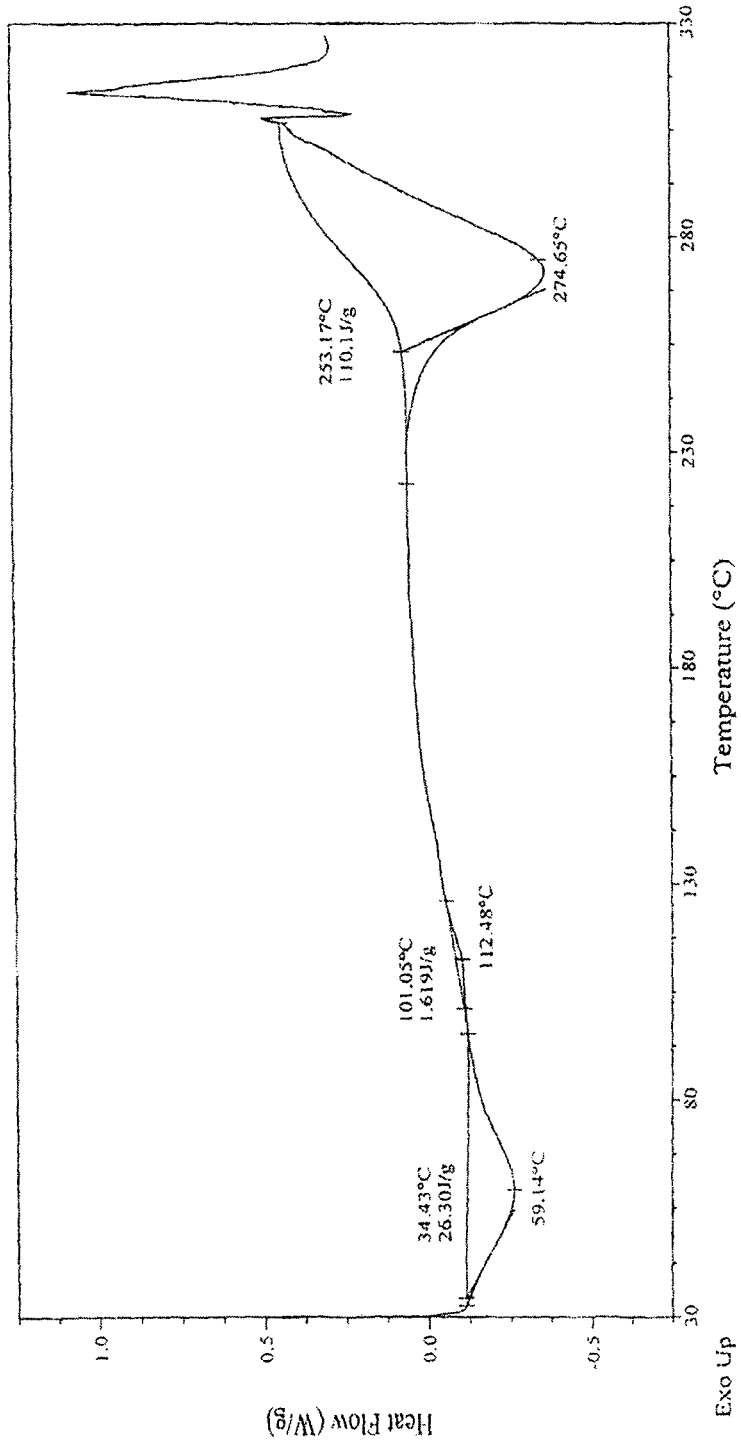
Fig 2 (DSc)

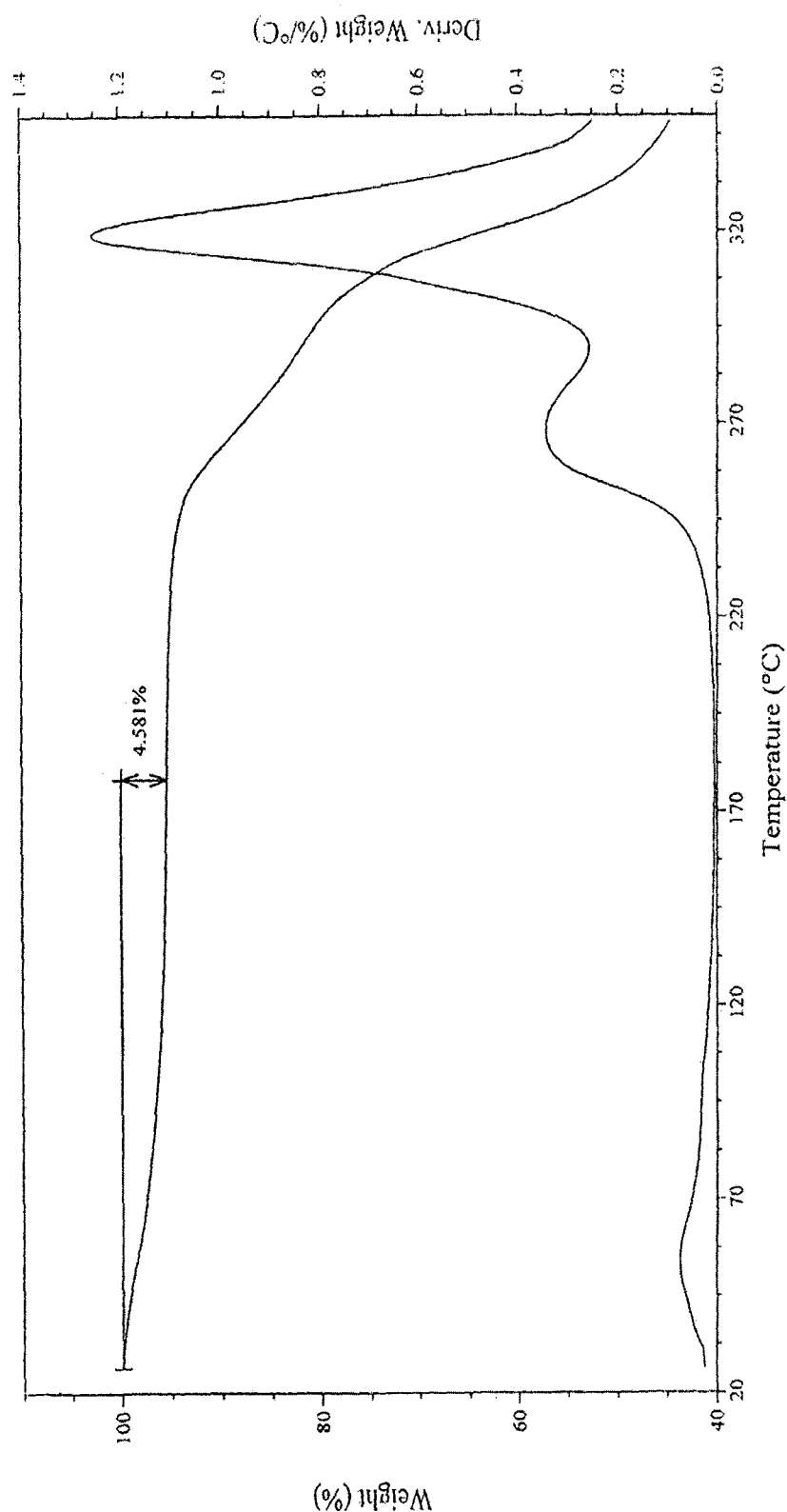
Fig. 3 (TGA)

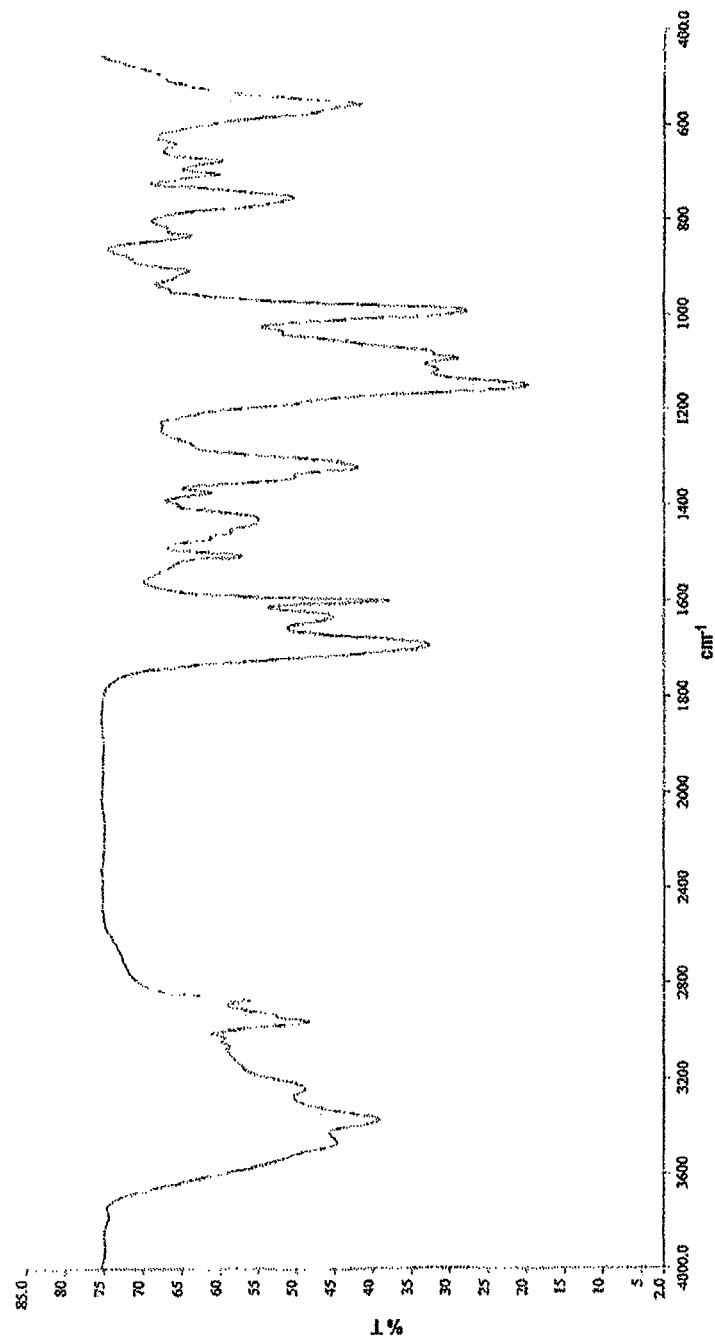
Fig. 4 (IR)

US 8,993,786 B2

CRYSTALLINE FOSAMPRENAVIR CALCIUM AND PROCESS FOR THE PREPARATION THEREOF

This application claims priority to Indian patent application No. 381/CHE/2011 filed on Feb. 10, 2011, the contents of which are incorporated by reference in their entirety.

FIELD OF THE INVENTION

The present invention relates to novel crystalline form of Fosamprenavir Calcium designated as Form A.

The present invention further relates to a process for the preparation of novel crystalline Form A of Fosamprenavir Calcium.

BACKGROUND OF THE INVENTION

Fosamprenavir Calcium is an antiviral compound, The chemical name of Fosamprenavir Calcium is Calcium (3S) tetrahydro-3-furanyl (1S,2R)-3-[[(4-aminophenyl)sulfonyl](isobutyl)amino]-1-benzyl-2-(phosphonooxy)propylcarbamate. Fosamprenavir Calcium has HIV aspartyl protease inhibitory activity and is particularly well suited for inhibiting HIV-1 and HIV-2 viruses. Moreover, Calcium (3S) tetrahydro-3-furanyl (1S,2R)-3-[[(4-aminophenyl)sulfonyl](isobutyl)amino]-1-benzyl-2-(phosphonooxy)propylcarbamate has increased solubility in the pH range of the gastro-intestinal tract compared to the HIV protease inhibitor [3S-[3R*(1R*,2S*)]]-[3-[[(4-aminophenyl)sulfonyl](2-methyl-propyl)amino]-2-hydroxy-1-phenylmethyl)propyl]-tetrahydro-3-furanyl ester (amprenavir, 141W94). Amprenavir, which has poor solubility and is thus available as a solution in gel capsules and has a high pill burden. This new HIV protease inhibitor with its increased solubility thus has the potential to reduce the perceived pill burden and may be formulated as a tablet.

The structure of Calcium (3S) tetrahydro-3-furanyl (1S,2R)-3-[[(4-aminophenyl)sulfonyl](isobutyl)amino]-1-benzyl-2-(phosphonooxy)propylcarbamate is shown below as Formula I

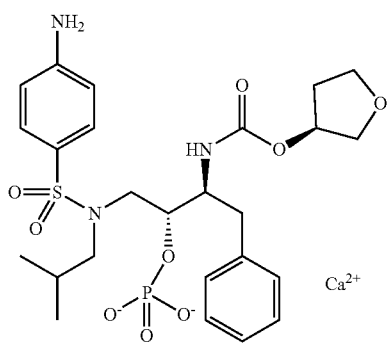

Formula I

U.S. Pat. No. 6,436,989B1 patent disclosed Fosamprenavir and its pharmaceutically acceptable salts, A wide range of salts of Fosamprenavir were made in this patent viz. di-sodium, di-potassium, magnesium, zinc, ethylene diamine, piperazine etc. Of these, the piperazine salt was a crystalline solid, but had the practical disadvantage of toxicity at the anticipated dose.

U.S. Pat. No. 6,514,953B1 patent disclosed crystalline form 1 of calcium salt of (3S)-tetrahydrofuran-3-yl(1S,2R)-3-[[(4-aminophenyl)sulfonyl](isobutyl)amino]-1-benzyl-2-(phosphonooxy) propylcarbamate.

WO2010134045 publication disclosed an amorphous Fosamprenavir Calcium and process for the preparation of amorphous Fosamprenavir Calcium.

WO 2011001383 publication disclosed crystalline form II of Fosamprenavir Calcium and a process for the preparation of crystalline form II of Fosamprenavir Calcium.

WO2011085130 publication disclosed rod like amorphous, form II, form III; form IV and form P.

OBJECT AND SUMMARY OF THE INVENTION

The main object of the present invention relates to novel crystalline form of Fosamprenavir Calcium designated as Form A.

Another object of the present invention relates to a process for the preparation of Crystalline Form A of Fosamprenavir Calcium.

Yet another object of the present invention relates to crystalline Form A of Fosamprenavir Calcium characterized by an PXRD diffraction having reflections at about 3.1±0.2, 4.4±0.2, 5.0±0.2, 6.3±0.2, 7.4±0.2, 8.0±0.2, 2Θ.

Yet another object of the present invention relates to a process for the preparation of crystalline Fosamprenavir Calcium Form A comprising the steps of;
a) dissolving Fosamprenavir Calcium salt in a solvent or mixture of solvents,
b) heating the reaction mass,
c) removing the solvent
d) adding a second solvent or mixture of solvents; and
e) isolating crystalline form A of Fosamprenavir Calcium Yet another object the present invention relates to a process for the preparation of crystalline Fosamprenavir calcium Form A comprising steps of;
a) suspending Fosamprenavir Calcium in a solvent or mixture of solvents,
b) heating the reaction mass,
c) removing the solvent,
d) adding a second solvent or mixture of solvents, and
  d) isolating crystalline Form A of Fosamprenavir Calcium.

In yet another object, the present invention relates to a process for the preparation of crystalline Form A of Fosamprenavir Calcium comprising the steps of
a) suspending Fosamprenavir Calcium in a solvent or mixture of solvents,
b) heating the reaction mass,
c) optionally cooling the reaction mass, and
d) isolating crystalline form A of Fosamprenavir Calcium.

Yet another object the present invention relates to a process for the preparation of crystalline Fosamprenavir calcium Form A comprising steps of;
a) suspending Fosamprenavir Calcium in a solvent or mixture of solvents,
b) heating the reaction mass,
c) seeding the reaction mass, and
d) isolating crystalline Form A of Fosamprenavir Calcium.

In yet another object, the crystalline form A of Fosamprenavir Calcium prepared according to the present invention is its hydrated form having moisture content of 2.5 to 5.5%.

BRIEF DESCRIPTION OF THE DRAWINGS

FIG. 1 depicts the X-ray powder Diffraction (XRPD) pattern of crystalline Form A of Fosamprenavir Calcium.

FIG. 2 depicts the Differential Scanning Calorimetry (DSC) thermogram of crystalline Form A of Fosamprenavir Calcium.

FIG. 3 depicts the TGA thermogram of crystalline Form A of Fosamprenavir Calcium.

FIG. 4 depicts the FT-IR spectra of crystalline Form A of Fosamprenavir Calcium.

INSTRUMENTATION DETAILS

Powder X-Ray Diffraction (PXRD)

The said formic acid solvate of the present invention is characterized by their X-ray powder diffraction pattern. Thus, the X-ray diffraction patterns of said polymorphs of the invention were measured on Bruker AXS D8 Discover powder X-ray diffractometer equipped with a goniometer of θ/2θ configuration, Variol monochromator and Lynx-Eye detector. The Cu-anode X-ray tube was operated at 40 kV and 30 mA. The experiments were conducted over the 2θ range of 2.0°-50.0°, 0.030° step size and 25 seconds step time.

Differential Scanning Calorimetry (DSC)

The DSC measurements were carried out on TA Q1000 of TA instruments. The experiments were performed at a heating rate of 10.0° C./min over a temperature range of 30° C.-200° C. purging with nitrogen at a flow rate of 50 ml/min. Standard aluminum crucibles covered by lids with three pin holes were used.

Thermo Gravimetric Analysis (TGA)

TGA/DTA was recorded using the instrument TA Q5000 of TA instruments. The experiments were performed at a heating rate of 10.0° C./min over a temperature range of 30° C.-300° C. purging with nitrogen at a flow rate of 25 ml/min.

Infrared Spectroscopy (IR)

Fourier transform infrared (FT-IR) spectra were recorded with a Perkin-Elmer spectrum one spectrometer. The samples were prepared as 1 mm thickness and 13 mm diameter KBr glassy discs by triturating 1 to 3 mg of sample with 300 mg to 400 mg of KBr and applying pressure of about 1000 lbs/sq inch. Then these discs were scanned in the spectral range of 4000 to 650 cm-1 with a resolution of 4 cm-1.

Karl-Fischer (KF)

Water content was determined on Metrohm karl-Fischer titrator (Model: 794 Basic Titrino) using pyridine free single solution (Merck, Mumbai) with sample mass between 450-550 mg.

DETAILED DESCRIPTION OF THE INVENTION

The present invention relates to novel crystalline form of Fosamprenavir Calcium designated as Form A.

In one embodiment, the crystalline Form A of Fosamprenavir Calcium is characterized by PXRD pattern as shown in FIG. 1.

In another embodiment, the present invention relates to crystalline Form A of Fosamprenavir Calcium characterized by an PXRD diffraction having reflections at about 3.1±0.2 2Θ, 4.4±0.2 2Θ, 5.0±0.2 2Θ, 6.3±0.2 2Θ, 7.4±0.2 2Θ, 8.0±0.2 2Θ.

In yet another embodiment, the present invention relates to crystalline Form A of Fosamprenavir Calcium characterized by DSC thermogram as shown in FIG. 2.

In yet another embodiment, the present invention relates to crystalline Form A of Fosamprenavir Calcium characterized by TGA/DTA thermogram as shown in FIG. 3.

In yet another embodiment, the present invention relates to crystalline Form A of Fosamprenavir Calcium as a hydrate with a moisture content of 2 to 5.5%.

In yet another embodiment, the present invention relates to crystalline Form A of Fosamprenavir Calcium characterized by FT-IR spectra with characteristic absorption bands (cm$^{-1}$) at 3467, 3373, 3062, 1690, 1317, 1147, 991, and 751 respectively; as depicted in FIG. 4.

In yet another embodiment, the process for the preparation of crystalline Fosamprenavir Calcium Form A comprising the steps of;
a) dissolving Fosamprenavir Calcium salt in a solvent or mixture of solvents,
b) heating the reaction mass,
c) removing the solvent,
d) adding a second solvent, and
e) isolating crystalline form A of Fosamprenavir Calcium According to the present invention, Fosamprenavir Calcium is dissolved in a solvent or mixture of solvents and heated the reaction mass to obtain clear solution. Removing the solvent results in a solid which is cooled and added with a second solvent. The resultant solid is filtered and dried to afford crystalline Form A of Fosamprenavir Calcium.

According to the present invention, fosamprenavir calcium is dissolved in a solvent selected from nitriles such as acetonitrile, propionitrile, acetone, methanol, ethanol, butanol, water or their mixtures thereof the second solvent is selected from ester solvents such as ethyl acetate, chlorinated solvents such as dichloromethane, chloroform; hydrocarbon solvents such as toluene, xylene, n-hexane, n-heptane, cyclohexane; esters such as ethyl acetate, n-propyl acetate, n-butyl acetate, t-butyl acetate; ethers such as methyl tertiary butyl ether, diethyl ether, dimethyl ether, diisopropyl ether; nitriles such as acetonitrile, propionitrile; water or their mixtures thereof.

In yet another object the present invention relates to a process for the preparation of crystalline Fosamprenavir calcium Form A comprising steps of;
a) suspending Fosamprenavir Calcium in a solvent or mixture of solvents,
b) heating the reaction mass,
c) removing the solvent,
d) adding a second solvent or mixture of solvents, and
d) isolating crystalline Form A of Fosamprenavir Calcium.

According to the present invention, Fosamprenavir Calcium is suspended in a solvent or mixture of solvents and heated the reaction mass to obtain clear solution. Removing the solvent completely and adding a second solvent followed by filtering the solid affords crystalline Form A of Fosamprenavir Calcium.

According to the present invention, fosamprenavir calcium is suspended in a solvent selected from nitriles such as acetonitrile, propionitrile, acetone, methanol, ethanol, butanol, water or their mixtures thereof and the second solvent is selected from chlorinated solvents such as dichloromethane, chloroform; hydrocarbon solvents such as toluene, xylene, n-hexane, n-heptane, cyclohexane; esters such as ethyl acetate, n-propyl acetate, n-butyl acetate, t-butyl acetate; ethers such as methyl tertiary butyl ether, diethyl ether, dimethyl ether, diisopropyl ether; nitriles such as acetonitrile, propionitrile, water or their mixtures thereof.

Yet another embodiment of the present invention relates to a process for the preparation of crystalline Form A of Fosamprenavir Calcium comprising the steps of
a) suspending Fosamprenavir Calcium in an solvent or mixture of solvents,
b) heating the reaction mass,
c) optionally cooling the reaction mass, and
d) isolating crystalline Form A of Fosamprenavir Calcium.

According to the present invention, Fosamprenavir Calcium is suspended in an organic solvent or mixture of solvents and heated the reaction mass to about 60 to 75° C. Optionally cooling the reaction mass and filtering affords crystalline Form A of Fosamprenavir Calcium.

According to the present invention, Fosamprenavir calcium is suspended in an organic solvent selected from ketones such as acetone, methyl isobutyl ketone, methyl ethyl ketone and cyclohexanone; alcohols such as methanol, ethanol, isopropanol, n-propanol, n-butanol, tertiary-butyl alcohol, cyclohexanol; chlorinated solvents such as dichloromethane, chloroform; hydrocarbon solvents such as toluene, xylene, n-hexane, n-heptane, cyclohexane; esters such as ethyl acetate, n-propyl acetate, n-butyl acetate, t-butyl acetate; ethers such as diethyl ether, dimethyl ether, diisopropyl ether or their mixtures thereof.

Yet another object the present invention relates to a process for the preparation of crystalline Fosamprenavir calcium Form A comprising steps of;
a) suspending Fosamprenavir Calcium in a solvent or mixture of solvents,
b) heating the reaction mass,
c) seeding the reaction mass, and
d) isolating crystalline Form A of Fosamprenavir Calcium.

According to the present invention, Fosamprenavir Calcium is suspended in an organic solvent or mixture of solvents and heated the reaction mass to about 60 to 75° temperature. Adding seed crystals of fosamprenavir calcium form A material and filtering affords crystalline Form A of Fosamprenavir Calcium.

According to the present invention, Fosamprenavir calcium is suspended in an organic solvent selected from ketones such as acetone, methyl isobutyl ketone, methyl ethyl ketone and cyclohexanone; alcohols such as methanol, ethanol, isopropanol, n-propanol, n-butanol, tertiary-butyl alcohol, cyclohexanol; chlorinated solvents such as dichloromethane, chloroform; hydrocarbon solvents such as toluene, xylene, n-hexane, n-heptane, cyclohexane; esters such as ethyl acetate, n-propyl acetate, n-butyl acetate, t-butyl acetate; ethers such as diethyl ether, dimethyl ether, diisopropyl ether, water or their mixtures thereof.

According to the present invention, Fosamprenavir calcium used as input is selected from Fosamprenavir calcium form I or Fosamprenavir calcium amorphous form.

In yet another embodiment, the Fosamprenavir Calcium prepared according to the present invention is its hydrated form have a moisture content of 2 to 7% preferably 3.0 to 5.5%

In yet another embodiment, the Fosamprenavir Calcium prepared according to the present invention has a HPLC purity of more than 99% preferably more than 99.8%.

In yet another embodiment, the Fosamprenavir calcium Form A shows no significant degradation, no substantial increase in moisture content and no change in PXRD pattern when stored for 6 months at different stress conditions as mentioned below in table 1. This indicates that Fosamprenavir Calcium Form A is physically and chemically stable.

In yet another embodiment, physical and chemical stability of Fosamprenavir calcium Form A was determined by storing the samples at 40° C./75% relative humidity (RH), at 25° C./60% RH and at 5° C. for 6 months. The material was analyzed by PXRD, water content by Karl Fischer and HPLC for final purity.

TABLE 1

| | at 40° C./75% RH | | | at 25° C./60% RH | | | at 5° C. | | |
| --- | --- | --- | --- | --- | --- | --- | --- | --- | --- |
| Condition | HPLC purity (%) | Water content (% w/w) | PXRD | HPLC purity (%) | Water content (% w/w) | PXRD | HPLC purity (%) | Water content (% w/w) | PXRD |
| Initial | 99.85 | 4.2 | Form A | 99.85 | 4.2 | Form A | 99.85 | 4.2 | Form A |
| 15 days | 99.84 | 3.5 | Form A | 99.85 | 3.7 | Form A | 99.85 | 3.6 | Form A |
| $1^{st}$ Month | 99.85 | 3.5 | Form A | 99.85 | 3.6 | Form A | 99.85 | 3.5 | Form A |
| $2^{nd}$ Month | 99.85 | 3.9 | Form A | 99.86 | 3.7 | Form A | 99.86 | 4.4 | Form A |
| $3^{rd}$ Month | 99.86 | 3.8 | Form A | 99.87 | 3.9 | Form A | 99.86 | 4.0 | Form A |
| $6^{th}$ Month | 99.86 | 3.0 | Form A | 99.85 | 3.5 | Form A | 99.86 | 3.5 | Form A |

In yet another embodiment, the physical stability of Fosamprenavir calcium Form A was determined by storing 1.0 g of sample at 50° C. and 80° C. under vacuum and at 90% relative humidity (RH). The samples are tested by PXRD after 15 hours and 72 hours. There is no change in polymorph observed in Form A under both drying and humidity conditions. Transformation kinetics of Form A was studied by suspending 1 g of Form A in appropriate solvents at 25-30° C. for 15 hours. The solid samples were characterized by PXRD.

Crystalline form A of Fosamprenavir Calcium is physically stable under different stress conditions. The results are shown in following Table 2.

TABLE 2

| Condition | Duration (h) | Result |
| --- | --- | --- |
| Drying at 50° C. | 15 | Form A |
| | 72 | Form A |
| Drying at 80° C. | 15 | Form A |
| | 72 | Form A |
| 90% RH | 15 | Form A |
| | 72 | Form A |
| Slurry in n-Heptane | 15 | Form A |
| Slurry in IPE | 15 | Form A |
| Slurry in ethyl acetate | 15 | Form A |
| Slurry in acetone | 15 | Form A |

The following examples are merely shown as representative examples of the present invention but are not intended to be limiting.

EXAMPLES

Example 1

Fosamprenavir Calcium (3 g) was suspended in acetonitrile (90 ml) at 25 to 30° C. The solution was heated to 70° C. to get clear solution. The clear solution was stirred for 15 hours at 70° C. The solid obtained was filtered and dried under vacuum at 40° C. for 1 hour. The product obtained was identified as Fosamprenavir Calcium novel form.

Example 2

Fosamprenavir Calcium (1 g) was suspended in acetonitrile (30 ml) at 25 to 30° C. The solution was heated to 70° C. to get clear solution. To the clear solution, seeds of Fosamprenavir Calcium novel form was added and stirred for 6 hours at 70° C. The solid obtained was filtered and dried under vacuum at 40° C. for 1 hour to afford Fosamprenavir Calcium Form A.

Example 3

Fosamprenavir calcium (0.5 g) was suspended in acetonitrile (5 ml) and acetone (5 ml) at 25 to 30° C. The solution was heated to 70° C. to get clear solution. To the clear solution, seeds of Fosamprenavir calcium novel form were added and stirred for 6 hours at 70° C. The solid obtained was filtered and dried under vacuum at 40° C. for to afford Fosamprenavir Calcium Form A.

Example 4

Fosamprenavir calcium (3 g) was suspended in acetonitrile (60 ml) at 25 to 30° C. The suspension was heated to 70° C. and stirred for 15 hours at 70 to 80° C. The suspension obtained was slowly cooled to 0 to 5° C. and maintained for 2 to 3 hours at 0 to 5° C. The solid obtained was filtered and dried under vacuum at 40° C. for 4 to 6 hours to afford crystalline Fosamprenavir calcium Form A.

Example 5

Fosamprenavir calcium (10 g) was suspended in acetonitrile (100 ml) at 25 to 30° C. The suspension was heated to 70 to 80° C. and stirred for 6 hours at 70 to 80° C. The suspension obtained was slowly cooled to 0 to 5° C. and maintained for 2 to 3 hours at 0 to 5° C. The solid obtained was filtered and dried under vacuum at 40° C. for 4 to 6 hours to afford crystalline Fosamprenavir calcium Form A.

Example 6

Fosamprenavir Calcium (10 g) was suspended in acetonitrile (150 ml) at 25 to 30° C. The suspension was heated to 70 to 80° C. and stirred for 6 hrs at 70 to 80° C. The suspension obtained was slowly cooled to 0 to 5° C. and maintained for 2 to 3 hours at 0-5° C. The solid obtained was filtered and dried under vacuum at 40° C. for 4 to 6 hrs to afford crystalline Fosamprenavir Calcium Form A.

Example 7

Fosamprenavir calcium (10 g) was suspended in acetonitrile (100 ml) and acetone (100 ml) at 25 to 30° C. The suspension was heated to 70 to 80° C. and stirred for 6 hours at 70 to 80° C. The suspension obtained was slowly cooled to 0-5° C. and maintained at 0-5° C. for 2 to 3 hours. The solid obtained was filtered and dried under vacuum at 40° C. for 4 to 6 hours to afford crystalline Fosamprenavir Calcium Form A.

Example 8

Fosamprenavir Calcium (3 g) was suspended in acetonitrile (15 ml) and acetone (30 ml) at 25-30° C. The suspension was heated to 70-80° C. and stirred for 2 to 3 hours at 70 to 80° C. The suspension obtained was slowly cooled to 0 to 5° C. and added acetone (30 ml) at 0 to 5° C. The solid obtained was filtered and dried under vacuum at 40° C. for 4-6 hours to afford crystalline Fosamprenavir Calcium Form A.

Example 9

Fosamprenavir calcium Form I (20 g) was suspended in acetonitrile (100 ml) at 25-30° C. The suspension was heated to 70-75° C. and maintained under agitation for 4 hours at 70-75° C. The resulting suspension was distilled off completely to remove solvent and then kept under vacuum for 30 minutes to 1 hour. The reaction mass was slowly cooled to 25-30° C., added methyl tertiary butyl ether (100 ml) and stirred for 2 hours at 25-30° C. The obtained solid was filtered, washed with methyl tertiary butyl ether (50 ml), dried at 50° C. under vacuum for 15 hrs. The solid obtained was identified as crystalline Fosamprenavir calcium Form A.

Example 10

Fosamprenavir calcium Form I (100 g) was suspended in acetonitrile (500 ml) at 25-30° C. The suspension was heated to 70-75° C. and maintained under agitation for 4 hours at 70-75° C. The resulting suspension was distilled off completely to remove solvent and then kept under vacuum for 30 minutes to 1 hour. To the reaction mass, acetonitrile (300 ml), ethyl acetate (800 ml) were added and stirred for 15 hours at 70-75° C. The suspension was slowly cooled to 0-5° C. and stirred for 1 hour at 0-5° C. The obtained solid was filtered, washed with ethyl acetate (200 ml) and dried at 50° under vacuum for 15 hours. The solid obtained was identified as crystalline Fosamprenavir calcium Form A.

Example 11

Fosamprenavir calcium Form I (50 g) was suspended in methanol (100 ml) and acetonitrile (200 ml) at 25-30° C. The solution was heated to 40-50° C. to obtain clear solution and maintained under agitation for 1 hour at 45-50° C. The clear solution was filtered through hy-flo and washed with acetonitrile (50 ml). The clear solution was distilled off completely at 60-65° C. to remove solvent and kept under vacuum for 30 minutes to 1 hour. To the reaction mass, acetonitile (250 ml) was added and heated to 70-75° C. The solvent was distilled off completely and kept under vacuum for 30 minutes to 1 hour. To the reaction mass, acetonitrile (150 ml), ethyl acetate (400 ml) were added and stirred for 15 hours at 70-75° C. The suspension was cooled to 0-5° C. and then stirred for 1 hour at 0-5° C. The obtained solid was filtered and washed with ethyl acetate (50 ml) and dried at 50° C. under vacuum for 15 hours. The solid obtained was identified as crystalline Fosamprenavir calcium Form A.

Example 12

Fosamprenavir calcium amorphous form (50 g) was dissolved in acetonitrile (250 ml) and water (4.0 ml) at 25-30° C.

The clear solution is heated to 70-75° C. and maintained under agitation for 4 h at 70-75° C. The solvent was distilled off completely at 70-75° C. and kept under vacuum for 030 minutes to 1 hour. The obtained solid is slowly cooled to 25-30° C. and added methyl tertiary butyl ether (250 ml) and stirred for 2 hours at 25-30° C. The obtained solid was filtered, washed with methyl tertiary butyl ether (50 ml) and dried at 50° C. under vacuum for 15 hours. The solid obtained was identified as crystalline Fosamprenavir calcium Form A.

Example 13

Fosamprenavir calcium amorphous form (50 g) was dissolved in acetonitrile (250 ml) and water (4.0 ml) at 25-30° C. The clear solution is heated to 70-75° C. and maintained under agitation the reaction mass for 4 hours at 70-75° C. The solvent was distilled off completely at 70-75° C. and kept under vacuum for 30 minutes to 1 hour. The obtained solid is slowly cooled to 25-30° C. and added acetonitrile (100 ml), ethyl acetate (200 ml) and stirred for 2 hours at 25-30° C. The obtained solid was filtered, washed with ethyl acetate (50 ml) and dried at 50° C. under vacuum for 15 hours. The solid obtained was identified as crystalline Fosamprenavir calcium Form A.

We claim:

1. Crystalline fosamprenavir calcium form A characterized by a powder X-ray diffraction pattern as shown in FIG. 1.

2. Crystalline fosamprenavir calcium form A having a powder X-ray diffraction pattern having at least one characteristic peak at 4.4±0.2, 5.0±0.2, 6.3±0.2, 7.4±0.2, or 8.0±0.2 2Θ.

3. A process for the preparation of crystalline fosamprenavir calcium form A comprising the steps of:
    a) dissolving fosamprenavir calcium salt in a solvent system;
    b) heating the resulting mixture;
    c) removing the solvent system;
    d) adding a solvent selected from methyl tertiary butyl ether, acetonitrile, esters and mixtures thereof; and
    e) isolating crystalline form A of fosamprenavir calcium.

4. The process according to claim 3, wherein the solvent system in step a comprises acetonitrile, methanol, ethanol, butanol, acetone, water or mixtures thereof.

5. Crystalline fosamprenavir calcium form A according to claim 1 or 3, characterized by a DSC thermogram as shown in FIG. 2.

6. Crystalline fosamprenavir calcium form A according to claim 1 or 3, characterized by a TGA thermogram as shown in FIG. 3.

7. Crystalline fosamprenavir calcium form A according to claim 1 or 3, characterized by an FT-IR spectra with characteristic absorption bands ($cm^{-1}$) at 3467, 3373, 3062, 1690, 1317, 1147, 991, and 751.

8. Crystalline fosamprenavir calcium form A having a moisture content between 3 and 5.5 percent.

9. A process for the preparation of crystalline fosamprenavir calcium form A comprising the steps of:
    a) suspending fosamprenavir calcium in a solvent system;
    b) heating the resulting mixture;
    c) removing the solvent system;
    d) adding a solvent selected from methyl tertiary butyl ether, acetonitrile, ethyl acetate, acetone, water and mixtures thereof; and
    e) isolating crystalline form A of fosamprenavir calcium.

10. The process according to claim 9, wherein the solvent system in step a comprises acetonitrile, acetone, ethyl acetate, methanol, methyl tertiary butyl ether or mixtures thereof and the solvent in step d is selected from methyl tertiary butyl ether, acetonitrile, ethyl acetate, acetone, water and mixtures thereof.

11. A process for the preparation of crystalline fosamprenavir calcium form A comprising the steps of:
    a) suspending fosamprenavir calcium in a solvent selected from acetonitrile, acetone, ethyl acetate, methanol and methyl tertiary butyl ether;
    b) heating the resulting mixture;
    c) optionally cooling the mixture;
    d) optionally seeding the reaction mixture; and
    e) isolating crystalline fosamprenavir calcium form A.

12. Crystalline fosamprenavir calcium form A according to claim 2, characterized by a PXRD diffraction pattern having reflections at about 4.4°±0.2°, 5.0°±0.2°, 6.3°±0.2°, 7.4°±0.2° and 8.0°±0.2° 2Θ.

13. Crystalline fosamprenavir calcium form A according to claim 12, further characterized by additional reflections at about 3.3°±0.2°, 9.0°±0.2°, 9.8°±0.2°, 10.3°±0.2°, 11.5°±0.2°, and 12.1°±0.2° 2Θ.

* * * * *